(12) United States Patent
Dominguez

(10) Patent No.: US 6,726,706 B2
(45) Date of Patent: Apr. 27, 2004

(54) SUTURE TAPE AND METHOD FOR USE

(76) Inventor: Steven Dominguez, 19 Bridington, Laguna Niguel, CA (US) 92677

( * ) Notice: Subject to any disclaimer, the term of this patent is extended or adjusted under 35 U.S.C. 154(b) by 216 days.

(21) Appl. No.: 09/891,914

(22) Filed: Jun. 26, 2001

(65) Prior Publication Data

US 2002/0198565 A1 Dec. 26, 2002

(51) Int. Cl.[7] .......................... A61B 17/04; A61L 17/00
(52) U.S. Cl. ................. 606/228; 606/148; 606/149; 606/150; 606/216; 606/228; 606/232; 606/233
(58) Field of Search ..................... 606/148, 149, 606/150, 216, 228, 232, 233; 602/41, 42, 52, 44, 60, 61, 62

(56) References Cited

U.S. PATENT DOCUMENTS

| | | | | |
|---|---|---|---|---|
| 2,008,361 A | * | 7/1935 | Lindsey | 229/87.05 |
| 4,222,383 A | * | 9/1980 | Schossow | 606/216 |
| 4,976,726 A | * | 12/1990 | Haverstock | 606/216 |
| 5,009,663 A | * | 4/1991 | Broome | 606/232 |
| 5,377,695 A | * | 1/1995 | An Haack | 128/888 |
| 5,534,010 A | * | 7/1996 | Peterson | 606/215 |
| 6,463,633 B1 | * | 10/2002 | Sangani et al. | 24/304 |

* cited by examiner

*Primary Examiner*—John J. Calvert
*Assistant Examiner*—Robert H. Muromoto, Jr.

(57) ABSTRACT

A tape for use in closing a tissue opening including a substrate and a plurality of sutures sewn directly into the substrate. The tape may have serrated edges in order to facilitate closure of a nonlinear tissue opening. Moreover, the tape may include windows in order to facilitate viewing of the tissue opening during closure and wound healing thereof. The sutures may be sewn laterally across the tape or not, and they may be imbedded individually into each side of the substrate, or they may be disposed under bridges between the windows in the substrate. The tape may have an adhesive affixed to one side thereof. Also disclosed is a method for closing a tissue opening by first cleaning the tissue; applying a layer of adhesive to the tissue adjacent to the opening; applying the tape over the opening; and, then tying each of the sutures together in order to pull the opening in the tissue closed.

11 Claims, 2 Drawing Sheets

SUTURE TAPE AND METHOD FOR USE

BACKGROUND OF THE INVENTION

1. Field of the Invention

The present invention relates to an improved type of suture tape and an improved method for using the same.

2. Description of Related Art

For centuries physicians have used stitches to close up gashes, cuts and surgical incisions in the skin tissue of patients. The medical techniques taught to and refined by the skill of the surgeon are basic; that is, the wound edges must be approximated and everted to allow for optimal wound closure and wound healing wherein both aid in producing acceptable cosmetic results. The traditional medical art of sealing up such tissue openings is to use sutures or stitches, which are literally sewn directly into the tissue. The sutures are then synched down to pull the tissue together for healing. The sewing of stitches directly into the skin adds further discomfort to the patient.

More recently, physicians have used glue or STERI-STRIPS®, or the like to close small or medium openings in the skin tissue. These techniques hold the parted tissue together, and are less painful to the patient, but they cannot be used to pull the tissue together as can be done with the original technique of sewing stitches into the skin. Problems identified with the use of glues increases scarring and abnormal wound healing due to poor approximation and lack of wound edge eversion performed by the surgeon or medical personnel. Leakage of the glue into the wound prevents adequate approximation and results in a widening of the scar as opposed to a fine line when traditional sutures are used. Likewise, the glue does not provide the mechanism for wound edge eversion, which is essential to the basic tenents of wound closure and optimal healing. STERI-STRIPS® and other tape-based wound closure instruments likewise do not provide for wound edge eversion. Hence, these devices fail to provide the patient with the proper basic tenets for wound closure and optimal wound healing.

Therefore, a need exists for a painless suture that can also pull the tissue together for healing. The present invention teaches the application of proper wound closure for optimal wound healing and is simple enough to be taught to the most basic of individuals. This invention in non-invasive and requires no anesthetic, as opposed to standard sutures in use today.

SUMMARY OF THE INVENTION

Accordingly, it is an object of the present invention to provide a simple means for skin closure following a gash, cut or surgical incision.

Another object of the present invention is to provide a satisfactory method and structure for closing skin that does not add further pain or uncomfort to the patient.

These and other objects, which will become apparent as the invention is described in detail below, are provided by a tape for use in closing a tissue opening including a substrate and a plurality of sutures sewn directly into the substrate. The tape may have serrated edges in order to facilitate closure of a nonlinear tissue opening. Moreover, the tape may include windows in order to facilitate viewing of the tissue opening during closure and wound healing thereof. The sutures may be sewn laterally across the tape or not, and they may be imbedded individually into each side of the substrate, or they may be disposed under bridges between the windows in the substrate. The tape may have an adhesive affixed to one side thereof. Also provided is a method for closing a tissue opening by first cleaning the tissue; applying a layer of adhesive to the tissue adjacent to the opening; applying the tape over the opening; and, then tying each of the sutures together in order to pull the opening in the tissue closed.

Still other objects, features and advantages of the present invention will become readily apparent to those skilled in the art from the following detailed description, wherein is shown and described only the preferred embodiment of the invention, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive, and what is intended to be protected by Letters Patent is set forth in the appended claims. The present invention will become apparent when taken in conjunction with the following description and attached drawings, wherein like characters indicate like parts, and which drawings form a part of this application.

BRIEF DESCRIPTION OF THE DRAWINGS

The general purpose of this invention, as well as a preferred mode of use, its objects and advantages will best be understood by reference to the following detailed description of an illustrative embodiment with reference to the accompanying drawings in which like reference numerals designate like parts throughout the figures thereof, and wherein.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide a new and improved skin closure suture and technique for use thereof.

Figure 1:
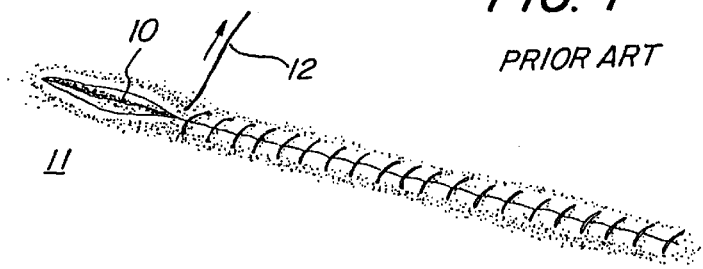
FIG. 1 illustrates the prior art technique for closing an opening in skin tissue.

Referring to the drawings and to FIG. 1 in particular, the prior art technique for skin closure is illustrated. A tissue opening 10 of skin 11 is being sewn up by the traditional technique of stitching the tissue opening 10 together with sutures 12. Note that once the suture is pulled taught, the skin 11 is puckered up. This puckering up is preferred for wound edge approximation and wound edge eversion.

Figure 2:
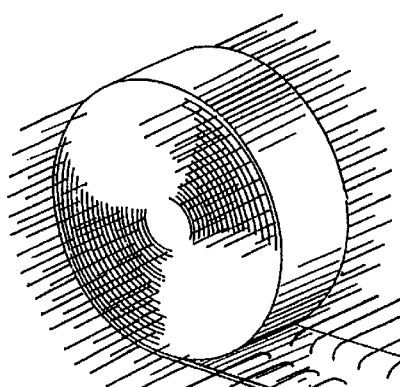
FIG. 2 illustrates a roll of skin closure tape in accordance with the teachings of the present invention.
Figure 3:
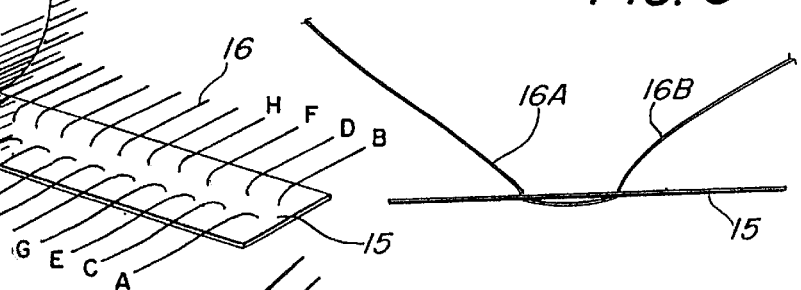
FIG. 3 illustrates an end view of the skin closure tape in accordance with the present invention.

Referring now to FIG. 2, a roll of tape 15 including sutures 16 is shown in accordance with one embodiment of the present invention. Individual sutures 16A–B, 16C–D, 16E–F, etc., are sewn directly into the tape 15 and are disposed for handy use when needed. FIG. 3 illustrates an end view of the tape 15 showing the suture 16A–16B.

Figure 4:
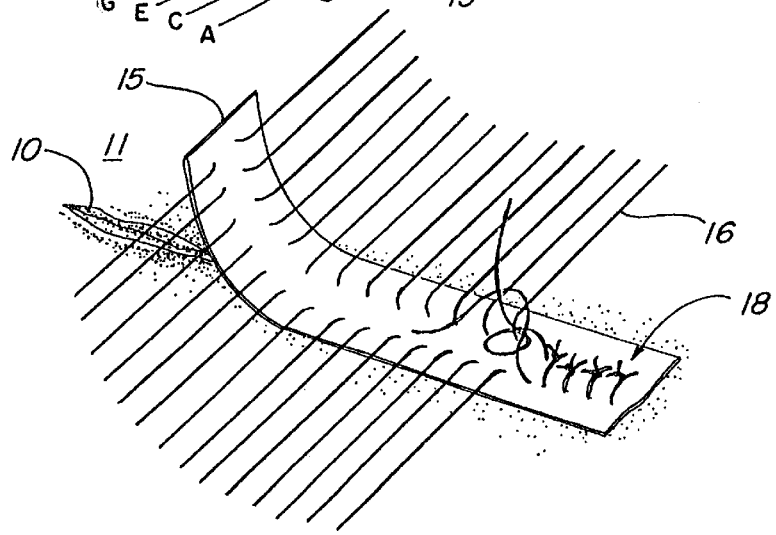
FIG. 4 illustrates the technique for skin closure in accordance with the teachings of the present invention.

Referring now to FIG. 4, the tape 15 is placed over the opening 10 in the skin 11 as shown. Before the tape 15 is placed over the skin 11, the skin is cleaned and an adhesive is applied, which helps the tape adhere to the skin. Conversely, the invention may have an adhesive backing that is uncovered prior to applying the tape to the skin. After this, the individual sutures 16A–16B, 16C–16D, etc. are tied together forming knots 18. This tying of the sutures pulls the skin together in a fashion identical to the method used in conventional sutures, thereby forming the skin puckering and closes the opening 10.

Figure 5:
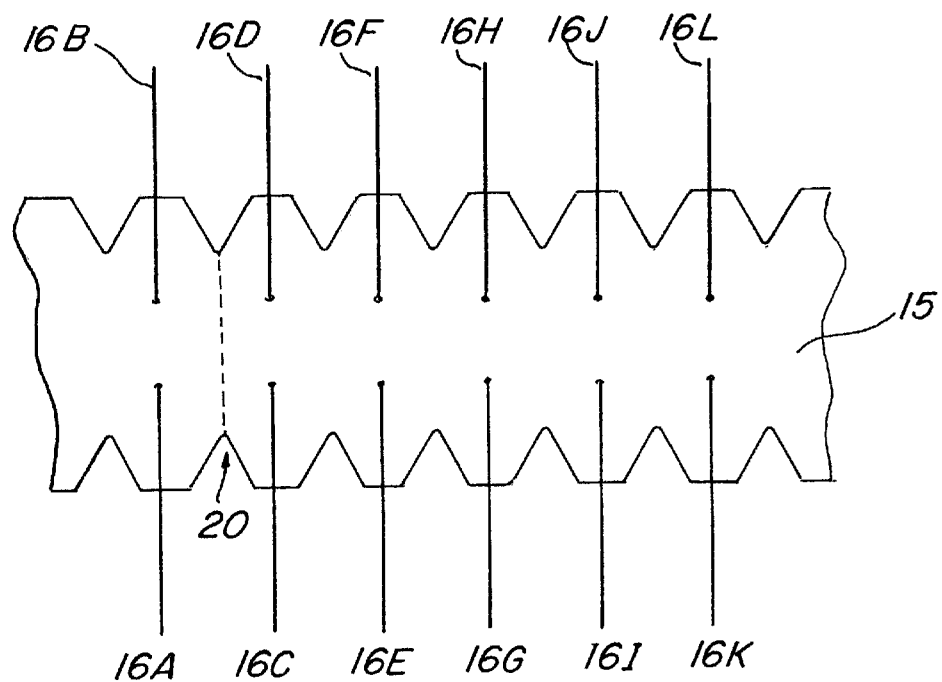
FIG. 5 illustrates the skin closure tape in accordance with an alternate embodiment of the present invention.

Referring now to FIG. 5, another embodiment of the present invention is shown. In this embodiment, the tape 15 has a serrated edge, which facilitates bending around serpiginous openings in the skin tissue. When a tissue opening is curved and not linear, it is much easier to bend the tape along the opening when the edges are serrated. An easy tear perforation 20 is made in the tape 15 at periodic intervals.

Figure 6:
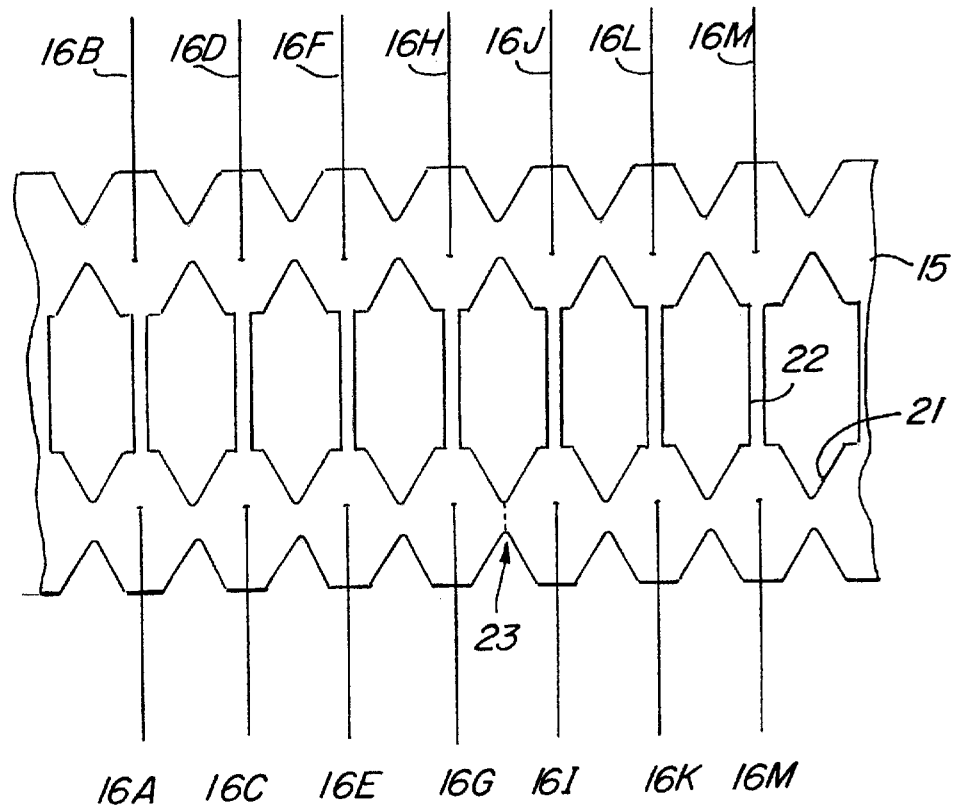
FIG. 6 illustrates the skin closure tape in accordance with a third embodiment of the present invention.

Referring now to FIG. 6, a preferred embodiment of the present invention is shown. In this embodiment, the edges are also serrated. However, windows 21 are made along the length of the tape 15 to facilitate viewing of the opening during closure and during wound healing. Note that each of the sutures, 16A–16B, 16C–16D, etc. are located beneath bridges 22 between each of the windows 21. Also, as in the previously-described embodiment easy tear perforations 23 are made periodically along the length of the tape 15.

Note that in all of the above-described embodiments, the structures may also be isolated and not necessarily traverse enblock from one side to the other, whereupon suture 16A is a stand alone suture and would not be adjoined to separate suture 16B, etc.

While the invention has been particularly shown and described with reference to a preferred embodiment, it will be understood by those skilled in the art that various changes in form and detail may be made therein without departing from the spirit and scope of the invention.

Those skilled in the art will appreciate that various adaptations and modifications of the just-described preferred embodiments can be configured without departing from the scope and spirit of the invention. Therefore, it is to be understood that within the scope of the appended claims, the invention may be practiced other than as specifically described herein.

What is claimed is:

1. A tape for use in closing a tissue opening, comprising:
   a. a substrate having a predetermined length and a predetermined width, the substrate having serrated edges along the length for placing the tape on a serpiginous tissue opening; and
   b. a plurality of sutures sewn into said substrate, spaced along the length and parallel to the width of the substrate.

2. The tape of claim 1 wherein the substrate has windows, which facilitate viewing of the tissue opening during closure and wound healing.

3. The tape of claim 2 wherein said sutures are disposed under bridges between each of the windows in said substrate.

4. The tape of claim 2 wherein each of said plurality of sutures comprise two separate lengths, with each individually on opposite sides of said substrate.

5. The tape of claim 1 wherein said substrate has an adhesive affixed to one side thereof.

6. The tape of claim 1 wherein the substrate is formed into a continuous finite length and wound up into a spool for convenient use.

7. The tape of claim 6 further having convenient tear perforations traversing the width of the tape spaced periodically along the length of said tape.

8. A method for closing a serpiginous tissue opening comprising the steps of:
   a. cleaning said tissue;
   b. applying a layer of adhesive to said tissue adjacent said opening;
   c. applying a tape of predetermined length and width with serrated edges along the length over said opening, the tape having a plurality of sutures sewn therein spaced along the length and parallel to the width of the tape; and,
   d. tying each of said sutures together as required to pull said tissue opening closed.

9. The method of claim 10 wherein said tape has an adhesive affixed thereto.

10. A method for closing a serpiginous tissue opening comprising the steps of:
    a. cleaning said tissue;
    b. applying a tape of predetermined length and width with serrated edges along the length over said opening, the tape having an adhesive affixed thereto and a plurality of sutures sewn individually therein spaced along the length and parallel to the width of the tape; and,
    c. tying each of said sutures together as required to pull said tissue opening closed.

11. The method of claim 10 wherein the tape includes windows spaced along the length of the tape to facilitate viewing the tissue opening during closure thereof.

* * * * *